United States Patent [19]

Smith et al.

[11] Patent Number: 5,755,793
[45] Date of Patent: May 26, 1998

[54] CENTRALIZER FOR A PROSTHETIC IMPLANT

[75] Inventors: William C. Smith, Columbia City; Kevin M. Greig, Leesburg, both of Ind.

[73] Assignee: Bristol-Myers Squibb Company, New York, N.Y.

[21] Appl. No.: 711,666

[22] Filed: Sep. 4, 1996

[51] Int. Cl.$^6$ ........................................................ A61F 2/28
[52] U.S. Cl. ................................................ 623/16; 623/23
[58] Field of Search ................................ 623/16, 18, 19, 623/20, 22, 23

[56] References Cited

U.S. PATENT DOCUMENTS

| | | | |
|---|---|---|---|
| Re. 28,895 | 7/1976 | Noiles | 3/1.912 |
| D. 339,865 | 9/1993 | Geremakis et al. | D24/155 |
| 3,793,650 | 2/1974 | Hewka et al. | 623/623 |
| 4,012,796 | 3/1977 | Weisman et al. | 3/1.91 |
| 4,065,817 | 1/1978 | Branemark et al. | 623/16 |
| 4,261,063 | 4/1981 | Blanquaert | 623/23 |
| 4,608,053 | 8/1986 | Keller | 623/23 |
| 4,650,489 | 3/1987 | Thompson | 623/18 |
| 4,661,112 | 4/1987 | Müller | 623/22 |
| 4,698,063 | 10/1987 | Link et al. | 623/23 |
| 4,718,909 | 1/1988 | Brown | 623/16 |
| 4,753,657 | 6/1988 | Lee et al. | 623/16 |
| 4,770,660 | 9/1988 | Averill | 623/23 |
| 4,813,960 | 3/1989 | Muller | 623/22 |
| 4,827,919 | 5/1989 | Barbarito et al. | 128/92 Y |
| 4,881,536 | 11/1989 | Noble et al. | 606/94 |
| 4,883,492 | 11/1989 | Frey et al. | 623/18 |
| 4,908,036 | 3/1990 | Link et al. | 623/23 |
| 4,995,883 | 2/1991 | Demane et al. | 623/23 |
| 4,997,448 | 3/1991 | Filer | 623/23 |
| 5,035,717 | 7/1991 | Brooks | 623/18 |
| 5,061,287 | 10/1991 | Feiler | 623/16 |
| 5,108,439 | 4/1992 | Morscher et al. | 623/18 |
| 5,108,452 | 4/1992 | Fallin | 623/23 |
| 5,116,377 | 5/1992 | Scripitz et al. | 623/23 |
| 5,116,380 | 5/1992 | Hewka et al. | 623/23 |
| 5,163,963 | 11/1992 | Hewka et al. | 623/23 |
| 5,314,493 | 5/1994 | Mikhail | 623/23 |
| 5,376,124 | 12/1994 | Gustke et al. | 623/23 |
| 5,507,831 | 4/1996 | Burke | 623/23 |
| 5,507,832 | 4/1996 | Michielli et al. | 623/23 |
| 5,531,793 | 7/1996 | Kelman et al. | 623/20 |

FOREIGN PATENT DOCUMENTS

| | | |
|---|---|---|
| 2 059 310 | 8/1992 | Canada . |
| 0 179 626 A2 | 4/1986 | European Pat. Off. . |
| 0 602 274 A1 | 6/1994 | European Pat. Off. . |
| 42 20 216 C1 | 1/1994 | Germany . |
| 2 104 391 | 3/1983 | United Kingdom . |

OTHER PUBLICATIONS

Mallory Head Hip Program—Biomet—Aug. 1989, Brit. JBJS.
Precision Strata™ Hip System—Howmedica—Mar. 1995, JBJS.
LSF Cemented Total Hip System—Implant Technology—Sep. 1991, JBJS.
OMNI/FIT®–C™ Femoral Stem System—Osteonics Corp.—c1991.
Hybrid Hip System—Smith & Nephew Richards—May 1993, JBJS.
Anatomic CC Hip—Zimmer, Inc.—c1992.

*Primary Examiner*—David Isabella
*Attorney, Agent, or Firm*—Margaret L. Geringer

[57] ABSTRACT

A centralizer 10 for positioning against a prosthetic implant 1. The centralizer 10 includes a plurality of inner raised ribs 15 extending from the inner surface 13 of the centralizer 10. The inner ribs 15 provide inner recessed pathways 16 which extend from the distal edge 12 toward the proximal edge 11. The centralizer 10 also may include a plurality of outer raised ribs 17. The inner and outer ribs 15 and 17 space the centralizer 10 from the implant 1 and the bone 5. This allows bone cement to flow into the gaps created between centralizer and the implant and between the centralizer and the bone.

18 Claims, 1 Drawing Sheet

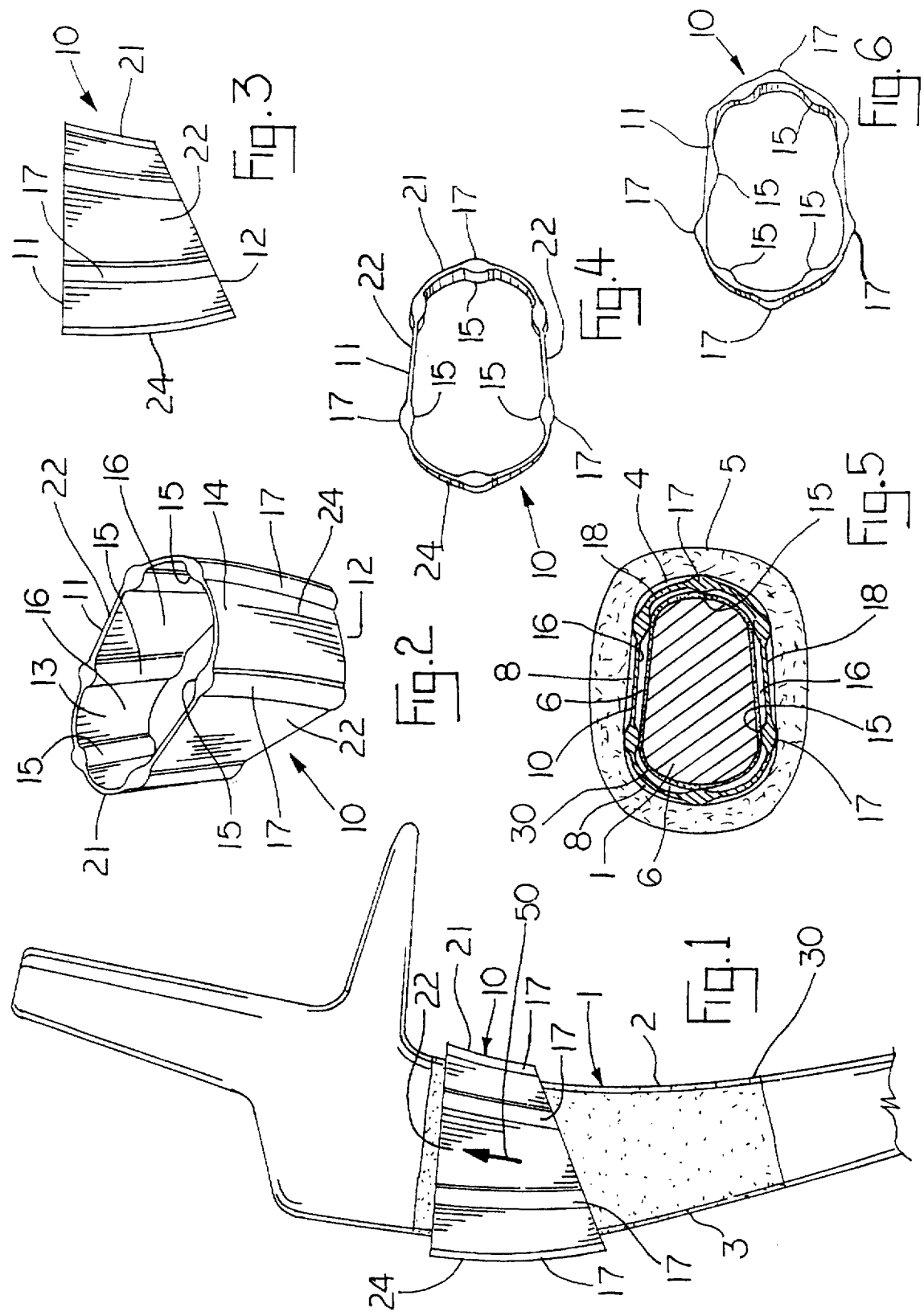

CENTRALIZER FOR A PROSTHETIC IMPLANT

FIELD OF THE INVENTION

The present invention relates to a centralizer, and in particular, to a centralizer for a prosthetic implant.

BACKGROUND OF THE INVENTION

In joint prostheses, centering devices or centralizers are used to position an implant stem, such as a femoral implant stem, within an intramedullary cavity. Centralizers typically position the implant stem so that the stem can be implanted into a bed of bone cement with a substantially uniform or predetermined thickness of cement surrounding the implant stem. Often a centralizer is used at both the proximal and distal end of an implant stem. Centering devices are well known and have been developed in a variety of shapes and configurations.

It is well known to provide centralizers with external ribs or fins to space the implant away from the bone cavity surface. Typically, the surface of the centralizer which contacts the implant is smooth. However, in U.S. Pat. No. 5,376,124, a spacer is provided to effectively extend the collar of the implant with the distal side of the spacer resting on the resected surface of the femur. The spacer includes spacer plugs and a ledge forming a lip along the distal edge of the spacer to form a cavity for receiving bone cement. The ledge captures the bone cement above it and holds the cement between the spacer and the proximal body and collar of a hip prosthesis until the cement sets to attach the spacer to the implant.

SUMMARY OF THE INVENTION

The present invention provides a centralizer for positioning against a prosthetic implant. The centralizer includes a plurality of inner raised ribs extending from the inner surface of the centralizer. The inner ribs provide inner recessed pathways which extend from the distal edge toward the proximal edge. The centralizer also may include a plurality of outer raised ribs. The inner and outer ribs space the centralizer from the implant and the bone. This allows bone cement to flow into the gaps created between centralizer and the implant and between the centralizer and the bone.

Accordingly, it is an advantage of the present invention to provide a novel centralizer which provides a gap between the centralizer and the implant to allow cement to flow between the centralizer and the implant upon insertion of the implant and centralizer into the cement.

Another advantage of the invention is to provide a simple, yet effective centralizer.

Still other advantages of the invention will become apparent upon reference to the accompanying drawings.

BRIEF DESCRIPTION OF THE DRAWINGS

FIG. 1 is a side view of the centralizer and corresponding prosthetic implant of the present invention.

FIG. 2 is a perspective view of the centralizer of FIG. 1.

FIG. 3 is a side view of the centralizer of FIG. 1.

FIG. 4 is a top view of the centralizer of FIG. 1.

FIG. 5 is a cross-sectional view of the centralizer and prosthetic implant of FIG. 1 positioned in a bone cavity.

FIG. 6 is a top view of an alternate embodiment of the centralizer of FIG. 1.

DESCRIPTION OF THE PREFERRED EMBODIMENT

FIGS. 1–6 illustrate particularly advantageous embodiments of the centralizer and prosthetic implant of the present invention. The invention will be described with reference to a prosthetic femoral stem implant 1; however, it is understood that it is not limited thereto.

In FIG. 1, centralizer 10 is positioned against the femoral stem implant 1 includes a centralizer 10 for positioning thereagainst. The centralizer 10 has a proximal edge 11 and a distal edge 12. The centralizer 10 includes a plurality of inner raised ribs 15 which extend from inner surface 13 to space the centralizer 10 away from implant 1. The inner ribs 15 provide inner recessed pathways 16 therebetween which extend from the distal edge 12 toward the proximal edge 11.

The centralizer 10 also includes a plurality of outer raised ribs 17 which extend from outer surface 14 of centralizer 10. The outer ribs 17 provide outer recessed pathways therebetween extending from the distal edge 12 toward the proximal edge 11.

The inner and outer ribs 15 and 17 are preferably elongated ribs which extend from about the distal edge 12 to about the proximal edge 11 of centralizer 10. As shown in FIGS. 2, 4, and 5, the outer ribs 17 are aligned with inner ribs 15. Alternatively, as shown in FIG. 6, the outer ribs 17 may be offset relative to inner ribs 15, if desired.

The centralizer preferably includes a first side 21 with two oppositely located sides 22 connected thereto. A fourth side 24 may be provided which is oppositely located from first side 21 and which extends between the two oppositely located sides 22 to form an enclosed ring. It is noted that an elongated slit (not shown) extending from the distal edge 12 to the proximal edge 11 may be provided, if desired. The distal edge 12 may be angled relative to the proximal edge 11, such that the first side 21, which is positioned against the medial side 2 of implant 1, is shorter in length than the fourth side 24, which is positioned against the lateral side 3 of implant 1. The centralizer is sized to fit at the desired location of the femoral stem implant 1. An arrow 50, as shown in FIG. 1, or other indicia may be provided on the centralizer 10 to indicate the direction of insertion of the centralizer 10 onto the tapered femoral stem implant 1.

The inner ribs 15 and inner recessed pathways 16 create inner gaps 6 between the centralizer 10 and implant 1 when positioned thereagainst, as shown in FIG. 5. The outer ribs 17 and outer recessed pathways 18 create outer gaps 8 between the centralizer and the bone 5 when the centralizer and implant are positioned in a corresponding cavity of bone 5. These inner and outer gaps 6 and 8 are designed to allow bone cement (not shown) to flow into the gaps 6 between the centralizer 10 and the implant 1 and into gaps 8 between the centralizer 10 and bone 5 upon insertion of the implant 1 and centralizer 10 into the cavity 4 of bone 5 which has been filled with bone cement.

The centralizer 10 is preferably made from an acrylic polymer, such as poly methyl methacrylate, so that upon insertion of the implant 1 and centralizer 10 into the bone cement, the polymer centralizer will repolymerize with the cement which has flowed into gaps 6 and 8 and which thus surrounds centralizer 10. The inner and outer gaps 6 and 8, which enable bone cement to flow therein upon insertion of the implant into a bone cement filled bone cavity 4, help provide more uniform and effective repolymerization of the polymer centralizer with the fresh bone cement. The femoral stem implant 1 may also include a polymer coating 30 of poly methyl methacrylate, such as that described in U.S. Pat.

No. 5,116,380 issued to Hewka et al. and incorporated herein by reference. The centralizer 10 may then be positioned on implant 1 adjacent coating 30 as shown in FIGS. 1 and 5. The fresh bone cement which flows into gaps 6 between centralizer 10 and the precoated implant 1, also helps provide more uniform and effective repolymerization of the polymer coating 30 with the fresh bone cement.

The inner and outer ribs 15 and 17 each preferably extend about one millimeter from inner and outer surfaces 13 and 14, respectively. Centralizer 10 helps to ensure that the femoral stem implant 1 is centered with the cavity 4 of bone 5 to provide a uniform layer of cement surrounding the femoral stem implant. However, the centralizer 10 may be shaped and dimensioned as desired. Also, any suitable manufacturing methods may be utilized.

While this invention has been described in terms of a particularly advantageous embodiment, those skilled in the art can appreciate that modifications can be made without departing from the spirit and scope of this invention.

We claim:

1. In combination, a prosthetic implant and a centralizer for positioning against the implant, the centralizer having a proximal edge and a distal edge, and an inner surface and an outer surface wherein a plurality of inner raised ribs extend from the inner surface of the centralizer to space the centralizer away from the implant the inner ribs providing inner recessed pathways therebetween which extend from the distal edge toward the proximal edge, and wherein the centralizer includes a plurality of outer raised ribs extending from the outer surface of the centralizer, the outer ribs providing outer recessed pathways therebetween extending from the distal edge toward the proximal edge, and wherein the outer ribs are aligned with the inner ribs.

2. The combination of claim 1 wherein the inner ribs are elongated ribs.

3. The combination of claim 2 wherein the inner elongated ribs extend from about the distal edge of the centralizer to about the proximal edge of the centralizer.

4. The combination of claim 1 wherein the outer ribs are elongated ribs.

5. The combination of claim 4 wherein the outer elongated ribs extend from about the distal edge of the centralizer to about the proximal edge of the centralizer.

6. The combination of claim 1 wherein the centralizer includes a first side with two oppositely located sides connected thereto.

7. The combination of claim 1 wherein the centralizer includes a fourth side oppositely located from the first side and extending between the two oppositely located sides forming an enclosed ring.

8. The combination of claim 1 wherein the inner ribs extend about one millimeter from the inner surface.

9. In combination, a prosthetic implant and a centralizer for positioning against the implant, the centralizer having a proximal edge and a distal edge, and an inner surface and an outer surface wherein a plurality of inner raised ribs extend from the inner surface of the centralizer to space the centralizer away from the implant, the the inner ribs providing inner recessed pathways therebetween which extend from the distal edge toward the proximal edge, and wherein the distal edge is not parallel to the proximal edge.

10. In combination, a prosthetic implant and a centralizer for positioning against the implant, the centralizer having a proximal edge and a distal edge, and an inner surface and an outer surface wherein a plurality of inner raised ribs extend from the inner surface of the centralizer to space the centralizer away from the implant, the inner ribs providing inner recessed pathways therebetween which extend from the distal edge toward the proximal edge, and wherein the centralizer is made from an acrylic polymer.

11. In combination, a prosthetic implant and a centralizer for positioning against the implant, the centralizer having a proximal edge and a distal edge, and an inner surface and outer surface wherein a plurality of inner raised ribs extend from the inner surface of the centralizer to space the centralizer away from the implant, the inner ribs providing inner recessed pathways therebetween which extend from the distal edge toward the proximal edge, and wherein the centralizer includes a plurality of outer raised ribs extending from the outer surface of the centralizer, the outer ribs providing outer recessed pathways therebetween extending from the distal edge toward the proximal edge, and wherein the outer ribs extend about one millimeter from the outer surface.

12. A centralizer for positioning against a prosthetic implant, wherein the centralizer has a proximal edge and a distal edge, and an inner surface and an outer surface, and wherein a plurality of inner raised ribs extend from the inner surface of the centralizer, the inner ribs providing inner recessed pathways therebetween which extend from the distal edge toward the proximal edge, and wherein the centralizer further includes a plurality of outer raised ribs extending from the outer surface of the centralizer, the outer ribs providing outer recessed pathways therebetween extending from the distal edge toward the proximal edge, and wherein the outer ribs are aligned with the inner ribs.

13. The centralizer of claim 12 wherein the inner ribs are elongated ribs which extend from about the distal edge of the centralizer to about the proximal edge of the centralizer.

14. The centralizer of claim 12 wherein the outer ribs are elongated ribs which extend from about the distal edge of the centralizer to about the proximal edge of the centralizer.

15. A method for centralizing a prosthetic implant relative to a bone surface comprising:

a) providing the prosthetic implant with an elongated stem portion;

b) providing a centralizer with a plurality of inner raised ribs extending from an inner surface of the centralizer;

c) positioning the centralizer about the elongated stem, such that the inner ribs cause the inner surface of the centralizer to be spaced from the implant forming an inner gap therebetween; and d) then subsequently inserting the implant and centralizer into a bone cavity already filled with a bone cement such that the bone cement flows into the inner gap between the implant and the inner surface of the centralizer upon such insertion.

16. The method of claim 15 further comprising providing the centralizer with a plurality of outer ribs extending from an outer surface of the centralizer in order to space the outer surface of the centralizer from the bone surface to form an outer gap therebetween, such that upon the insertion step, the bone cement flows into the outer gap between the bone surface and the outer surface of the centralizer.

17. The method of claim 15 further comprising providing a polymer coating on the implant, such that the positioning step further provides for positioning the centralizer about the stem adjacent the polymer coating such that upon inserting the implant, the bone cement flows into the inner gap between the polymer coating on the implant and the inner surface of the centralizer.

18. A method for centralizing a prosthetic implant relative to a bone surface comprising:

a) providing the prosthetic implant with an elongated stem portion;

b) providing a centralizer with a plurality of inner raised ribs extending from an inner surface of the centralizer;

c) positioning the centralizer about the elongated stem, such that the inner ribs cause the inner surface of the centralizer to be spaced from the implant forming an inner gap therebetween; and d) inserting the implant into a bone cavity filled with a bone cement such that the bone cement flows into the inner gap between the implant and the inner surface of the centralizer, and e) manufacturing the centralizer from an acrylic polymer.

* * * * *